United States Patent [19]

Baldacci et al.

[11] Patent Number: 5,470,965

[45] Date of Patent: Nov. 28, 1995

[54] COMPLEXABLE HETEROGENOUS OLIGOSACCHARIDES AND ALPHA-HYDOSANES HAVING THERAPEUTICAL ACTIVITY, PROCESS FOR THEIR PREPARATION AND RELATED PHARMACEUTICAL COMPOSITIONS

[75] Inventors: Massimo Baldacci; Ugo Baldacci, both of Pisa, Italy

[73] Assignee: Laboratori Baldacci Spa, Pisa, Italy

[21] Appl. No.: 554,972

[22] Filed: Jul. 17, 1990

Related U.S. Application Data

[63] Continuation of Ser. No. 296,913, Jan. 12, 1989, abandoned, which is a continuation of Ser. No. 628,421, Jul. 6, 1984, abandoned.

[30] Foreign Application Priority Data

Jul. 13, 1983 [IT] Italy .................................. 22045/83

[51] Int. Cl.$^6$ ................................................. C08B 37/10
[52] U.S. Cl. ........................................... 536/21; 536/18.7
[58] Field of Search ..................... 536/21, 18.7; 514/56, 514/54

[56] References Cited

U.S. PATENT DOCUMENTS

| | | | |
|---|---|---|---|
| 4,401,662 | 8/1983 | Lormeau et al. | 536/21 |
| 4,486,420 | 12/1984 | Lormeau et al. | 536/21 |
| 4,496,550 | 1/1985 | Lindahl et al. | 514/56 |

FOREIGN PATENT DOCUMENTS

| | | | |
|---|---|---|---|
| 0097625 | 1/1984 | European Pat. Off. . | |
| 2002406 | 2/1979 | United Kingdom | 536/21 |

OTHER PUBLICATIONS

Roden, L. 1980: In the Biochemistry of Glycoproteins and Proteoglycans, Ed. W. J. Lenners, pp. 267–371.
Lindhal et al, 1980 Proc. Natl. Acad. Sci. USA 77:6551–6555.
Casu et al, 1981 Biochemistry Journal, vol. 197 pp. 599–609.
Callagher et al; 1985 Biochemistry Journal, vol. 230, pp. 665–674.
Linker, Biochem J. vol. 183, (1979) pp. 711–720.
Nagasawa, K. et al "Hydrophobic Interaction Chromatography of Glycosaminoglycuronans . . . " Carboyhydrate Research, 111 (1983) 273–281.
Casu, B. et al "Fractionation and Characterization of Glycosaminoglycans of Mammalian Origin", Pharmacological Research Communications, vol. 11, No. 4, 1979, pp. 297–309.

*Primary Examiner*—Douglas W. Robinson
*Assistant Examiner*—Elli Peselev
*Attorney, Agent, or Firm*—Nikaido, Marmelstein, Murray & Oram

[57] ABSTRACT

Complexable heterogeneous oligosaccharides and pure alpha-hydosanes, namely not contaminated from other macromolecules (mucopolysaccharides, proteins, nucleic acids, etc.) of a defined molecular weight are produced starting from a mixture of mucopolysaccharides obtained starting from bovine or swine mucosa through a process comprising a precipitation with organic solvents, a further purification by means of specific enzymes and chromatographic separation by gel filtration. Heterogeneous oligosaccharides are obtained which can be complexed with metals, being thus able to promote the pharmacological effect of the metal thanks to the geater permeability towards the complexes of the membrane of the cells of the absorbing mucosa and of the cells of the target tissue. There are also obtained pure alpha-hydosanes having a well defined molecular weight range capable of providing several pharmacological activities more particularly an activating effect of he anti-thrombine III, a potentiating effect of the tissutal activator and a fibrine depolymerizing effect have been found for some of them whereas for some others an effect on the factor Xa/PTT ratio has been revealed and lastly for still others a lipasemic and anti-coagulating activity has been found.

3 Claims, 4 Drawing Sheets

COMPLEXABLE HETEROGENOUS OLIGOSACCHARIDES AND ALPHA-HYDOSANES HAVING THERAPEUTICAL ACTIVITY, PROCESS FOR THEIR PREPARATION AND RELATED PHARMACEUTICAL COMPOSITIONS

This application is a continuation of application Ser. No. 296,913, filed on Jan. 12, 1989, abandoned, which is a continuation of Ser. No. 628,421, filed on Jul. 6, 1984, abandoned.

The present invention relates to complexable heterogeneous oligosaccharides and to pure-alpha hydrosanes.

It is known that, in the processes for the heparin production, mixtures of natural mucopolysaccharides are obtained, which for some time have found therapeutical use in the treatment of atherosclerosis, peripheral artheropathies, alterations of the lipidic metabolism and the like.

These mixtures of mucopolysaccharides, prevailingly obtained by extraction from bovine and swine intestinal mucosa, contain condroitin, sulphates, dermatan sulphates, keratan sulphates, heperan sulphates, low title herapin and other substances.

In these mixtures the family of interest for the present invention consists of the natural heparan sulphates, having molecular weight of between 5000 and 60,000. In fact it is from this family that, according to the present invention oligosaccharides are isolated which can be complexed with salts of polyvalent metals, such as for example iron and copper, so as to promote the pharmacological activity of the metal, and a series of alpha-hydosanes is fractionated having a defined molecular weight and which show a number of pharmacological activities ranging from an interaction with the fibrinolithic, coagulating an thrombolithic process, to an anticoagulating activity, to a lipasemic activity and lastly to an interaction with the anti Xa/TTPA ratio and thus with the anti-thrombotic activity.

Another object of the present invention resides in the preparation process and mainly in the process for the fractionation and the purification of the above mentioned components.

It is known that the mixtures of mucopolysaccharides are obtained as by-products of the heparin production and involve a number of fractionating and purifying treatments which can be resumed as follows:

1) defatting and grinding of the bovine and swine intestinal mucosa;
2) enzymatic (pancreatinic) lysis;
3) coagulation of the protein fraction by acidifying;
4) separation of the protein components;
5) forming complexes of the mucopolysaccharides;
6) cleavage of the complex by treatment with NaCl;
7) purifying by removing the nucleic acids;
8) precipitating the mucopolysaccharides;
9) purifying the mucopolysaccharides.

The thus obtained mixture of mucopolysaccharides can be thereafter subjected to the adsorption and the separation of heparan sulphates, for instance by enzymatic (condroitinase) or chemical methods, The process according to the present invention essentially comprises subsequent steps of precipitation with organic solvents, purification with specific enzymes and chromatographic separation by gel filtration. More specifically the process according to the present comprises the following steps:

a) separation by solvent of the mixture of mucopolysaccharides in a first fraction, containing dermatan sulphate and several contaminating products, and in a second fraction, containing heparan sulphates, condroitin sulphate A and dermatane type contaminants;

b) solvent separation of said second fraction respectively in third fraction containing heparan sulphates including contaminants consisting of condroitin sulphate A and dermatanes, and in fourth fraction containing condroitin sulphate A;

c) conversion of the heparan sulphates contained in said third fraction from calcium salts to sodium salts;

d) preparation of polysaccharidases induced in Flavobacterium by fermentation in a culture medium added with said first and fourth fractions respectively, containing dermatan sulphate and condroitin sulphate A, and separation of the resulting enzymes, formed by polysaccharidases;

e) addition of said enzymes to said third fraction, in the presence of antibacteria agents, polysaccharide contaminants being thus removed from said heparan sulphates contained in said third fraction;

f) passing of the resulting purified fraction on a resin column equilibrated with a saline solution of low ionic force, whereby oligosaccharides having ,molecular weight of between 5400 and 1802, are retained onto the resin (thus forming the sixth fraction) and a fifth fraction consisting of purified heparanes is separated;

g) passing said fifth fraction through a gel filtration column, equilibrated with the same saline solution, whereby ten fractions are obtained, consisting of alpha-hydosanes having average molecular weight expressed as daltons of between 34,000 and 7,500 according to the following distribution:

| No. alpha-hydosanes | Average molecular weight (daltons) |
|---|---|
| 1 | 34000 |
| 2 | 20000 |
| 3 | 14600 |
| 4 | 13500 |
| 5 | 12300 |
| 6 | 10500 |
| 7 | 8600 |
| 8 | 7900 |
| 9 | 7500 |
| 10 | 7000 | h) forming the complexes between the oligosaccharides contained in said sixth fraction, removed from the resin and converted to their acidic form, and salts of polyvalent metals.

Specifically, the instant invention is directed to A) a substantially pure fraction of heparan sulfate haivng an average molecular weight range of from 12.3 kd to 10.5 kd and fibrinolytic activity, but substantially no anticoagulant activity and no antilipemic activity, B) a substantially pure fraction of heparan sulfate having an average molecular weight range of 7.0 kd to 8.6 kd and antithrombolytic activity, but substantially no anticoagulant activity and no antilipemic activity and C) a substantially pure fraction of heparan sulfate having an average molecular weight range of from 7.0 kd to 13.5 kd and at least one activity selected from the group consisting of fibrinolytic activity and antithrombolytic activity, but substantiallly no anticoagulant activity and no antilipemic activity.

According to the preferred embodiment of the process of the present invention, a mixture of mucopolysaccharides of swine or bovine intestinal mucosa is the starting mixture, containing dermatan sulphates, condroitin sulphates, heparan sulphates and heparins, protein contaminants, nucleic acids and other substances.

The mixture is cold dissolved in 0.5M calcium acetate and 0.5M acetic acid, at the concentration of 20 g/lt, and then ethanol is added until a final concentration of 20% is obtained. The mixture is filtered on a celite support. Dermatan sulphate (first fraction) and the several contaminants remain on the filter. To the clear filtrate forming the second fraction, containing heparan sulphates, condroitin sulphate A and dermatanes as impurities, cold ethanol is added until a concentration of 35% is attained. The mixture is decanted for few hours and then filtered again on celite. Heparan sulphates, contamined with dematane and traces of condroitin A, forming the said third fraction, are retained on the filter, whereas the filtrate does mainly contain condroitin sulphate A (fourth fraction).

The first fraction (dermatan sulphate) and the fourth fraction (condroitin sulphate A) are used to induce specific polysaccharidases in bacteria of the type Flavobacterium Heparium which shall be afterwards used for the subsequent purification of the heparan sulphates.

The precipitate of heparan sulphates, (remaining on the filter and forming the third fraction) is dissolved again in water and precipitated with two volumes of ethanol after addition of an amount of sodium chloride sufficient to give 1M, to convert the polysaccharides from calcium salts to sodium salts.

The precipitate is made anhydrous through subsequent additions of ethanol or acetone and oven dried under vacuum at 65° to 70° C.

There are thus obtained the partially purified heparanes, namely purified from most of dermatane and of the condroitins as well as form the macromolecular impurities contained in the starting product.

Preparation of the Polysaccharidases Induced in Flavobacterium

To a suspension of Flavobacterium in a culture medium dermatan sulphate (first fraction) and condroitin sulphate A (fourth fraction) are added at a total concentration of 5 g/l. The bacterial suspension is maintained for 48 hours at room temperature under strong aeration.

After proliferation the bacteria are settled by low speed centrifugation; the settled mass is suspended again in a saline solution and the cells are fragmented by means of ultrasonic waves and centrifuged at high speed to be freed from cellular fragments. The enzymes contained in the supernatant phase are precipitated by adding two volumes of acetone and thereafter made anhydrous through subsequent washing with acetone.

The thus obtained acetonic powder, which contains the whole necessary enzymatic range, is used for the next heparan sulphate purification.

Heparan Sulphate Purification

The raw heparan sulphate (third fraction) is dissolved in a saline solution buffered at an about neutral pH and at a concentration of between 10 and 30 g/l.

The solution is added with the raw enzymes induced as above described.

The mixture is incubated at $\leq 30°$ C., in the presence of antibacterial agents (p-chlorocresol, benzoic acid, etc.) for a time sufficient for the complete elimination of the contaminating polysaccharides (DS, CSA).

The elimination pattern is monitored through electophoresis on cellulose acetate, using barium acetate at pH 5 as buffer.

Upon the phase of elimination of the contaminating polysaccharides is completed, the whole mixture is passed through a G 50 or G 75 Sephadex column equilibrated with a saline-solution of low ionic force.

The portion excluded from the gel, containing the purified heparan sulphate (fifth fraction) is precipitated with ethanol and made anhydrous as previously described.

The components retained in the gel, containing the cleavage products of condroitins A and B, owing to the action of condroitinases, is passed through a Chelex 100 column equilibrated with distilled water in order to eliminate the traces of contaminants of calcium and of other polyvalent cations.

The eluate from the Chelex column is passed through an AC 50-W-XB column ($H^+$ form), eluted with distilled water, whereby the oligosaccharides are thus converted to their acidic form.

Moreover the proteic contaminants which remain bonded to the resin are thus also eliminated.

The thus obtained oligosaccharides can be subdivided in the following classes:

disaccharides, having molecular weight of between 540 and 620;

tetrasaccharides, having molecular weight of between 1060 and 1220, and hexasaccharides, having molecular weight of between 1580 and 1820.

Each class does contemplate further combinations as a function of the sulphatation degree whereby for the disaccharides two combinations exist, for the tetrasaccharides four combinations and six combinations for the hexasaccharides.

Thus, in ode to individuate the subject oligosaccharides, they can be defined as a function of the source, from condroitin and from dermatan, whereas their recognition can be carried out by gel filtration on superfine G 50 or G 75 columns against purified standards.

Oligosaccharide Salification (e.g. Di-, Tetra- and Hexasaccharides)

The thus obtained oligosaccharides are complexed with salts of polyvalent metals (e.g. ferrous and ferric ion, rameic, etc.), thanks to their polyanionic properties. To this end the acid oligosaccharides are treated with salts of polyvalent cations with organic or inorganic anions, and then precipitated with suitable and anydrified solvents.

Fractionation of Alpha-hydosanes

The said fifth fraction in purified form is dissolved in a saline solution having high ionic force (e.g. 4M GU HCl) at a neutral pH and fractionated in a column for gel filtration (e.g. G-100 Sephadex, and S-200 Sephacryl) equilibrated with the same saline solution. The flow rate is adjusted so as to get an optimum fractionation of the starting compounds.

The thus obtained fractions are collected by means of a fraction collector and then desalified on a G 50 Sephadex column equilibrated with saline solution of low ionic force.

The resulting fractions are precipitated with ethanol and made anhydrous as above described.

From the aforesaid fractionation 10 alpha-hydosanes are obtained of a defined molecular weight, precisely:

| No. alpha-hydosane | Average molecular weight (dalton) |
| --- | --- |
| 1 | 34000 |
| 2 | 20000 |
| 3 | 14600 |
| 4 | 13500 |
| 5 | 12300 |
| 6 | 10500 |
| 7 | 8600 |
| 8 | 7900 |
| 9 | 7500 |
| 10 | 7000 |

The molecular weights were determined as follows:

In a column (100 cm×1 cm) of superfine 2–200 Sephacryl, equilibrated with 4M guanidine chloride, 10 mg per each alpha-hydosane were used. The elution was carried out with the same solution of guanidine chloride, with a flow rate of 7 ml/h; the fractions collected in the collector were diluted in a ratio of 1:5 with water and portions of 100 µl each one were subjected to the dosage of the uronic acids with the method of the orcinol.

The resulting points were graphically interpolated by means of polynomial regression and from the average volume of elution of each peak the Kav factor was calculated, which was compared with a calibrating right line (Kay/1 g PM) obtained using dextranes having a defined molecular weight.

The method for the determination of the molecular weights has been described since it is the chemical-physical parameter by which the claimed alpha-hydosanes are characterized.

The other chemico-physical constants (e.g. iduronation degree, sulphatation degree) are not defined as being not remarkable; however it can be stated that said constants oscillate for all the compounds around an average value corresponding to that of the starting product. The compounds of the present invention have been subjected to pharmacological experiments by which the basic therapeutical indication have been respectively individuated.

I Pharmacological Tests of the Complex Salts of the Oligosaccharides (e.g. Di- and Tetra-saccharides).

The method for obtaining oligosaccharides from the cleavage products of the condroitinases and the synthesis method of the complex salts with the metals have been above described, among which the following are for example reported:

Compounds:

I complex salt with ferrous ion

II complex salt with ferric ion

III complex salt with cuprous ion

IV complex salt with cupric ion

V complex salt with auric ion

Without having limiting sense it seems plausible that the pharmacological principle at the basis of the realization of the preceding compounds is based on the hypothesis that the oligosaccharide, by coming into contact with the related receptor of cellular membrane, does transport the complexed ion by facilitating the incorporation of the metal by endocytosis, the transport thereof being thus facilitated at the level of the blood stream.

Consequently those compounds should permit a better bioavailability of the metal. To this end an analysis of the absorption has been carried out, after oral administration in the rat, of the ferrous oligosaccaridate (compound I) in comparison with ferrous sulphate at equimolar doses of ferrous ion.

To carry out the quantitative determination of the absorbed ion the two test compounds have been administered in a form marked with $^{59}Fe$ (one radioactive part for $3.10^6$ cold parts).

The analysis of the radioactivity after administration of the two compounds (d.p.m.) has revealed that the compound I (ferrous oligosaccharidate) is more readily absorbed, with an increase of the hematic levels by 40% with respect to the administration of ferrous sulphate used for comparison purposes.

On the basis of what already demonstrated and on the basis of the assumptions on the action mechanism it can be stated that also the other ions in the form of complex salts with oligosaccharides follow the same metabolic route.

Consequently the use of these compounds is foreseen in the therapy of pathogenesis induced by want of the several metals or of their pharmacological properties:

compounds I and II in the anaemia induced by iron want, compounds III, IV and V in the case of arthroheumopathies.

II Pharmacological Testing of Alpha-hydosanes 10 compounds (alpha-hydosanes) obtained and characterized as previously described have been analyzed from the pharmacological point of view by singularly evaluating their interaction with the fibrinolithic coagulating thrombolithic process and with the lipidic metabolism.

The fibrinolithic action has been evaluated in vitro on platelets of human fibrine containing activators (according to Astrup) by controlling the lysis halo induced by applying the test compound as a solution to the surface.

BRIEF DESCRIPTION OF THE DRAWINGS

The behaviour of the activity for the several compounds is reported in FIG. 1 from which it can be observed that the alpha-hydosanes Nos 5 and 6 are endowed with high fibrinolithic activity which is significatively higher than the other compounds having different molecular weight.

The anticolagulating activity in comparison with heparin (HP) has been evaluated as the increase of the coagulation time of the rabbit plasma in vitro, induced by calcium chloride.

Figure 1:
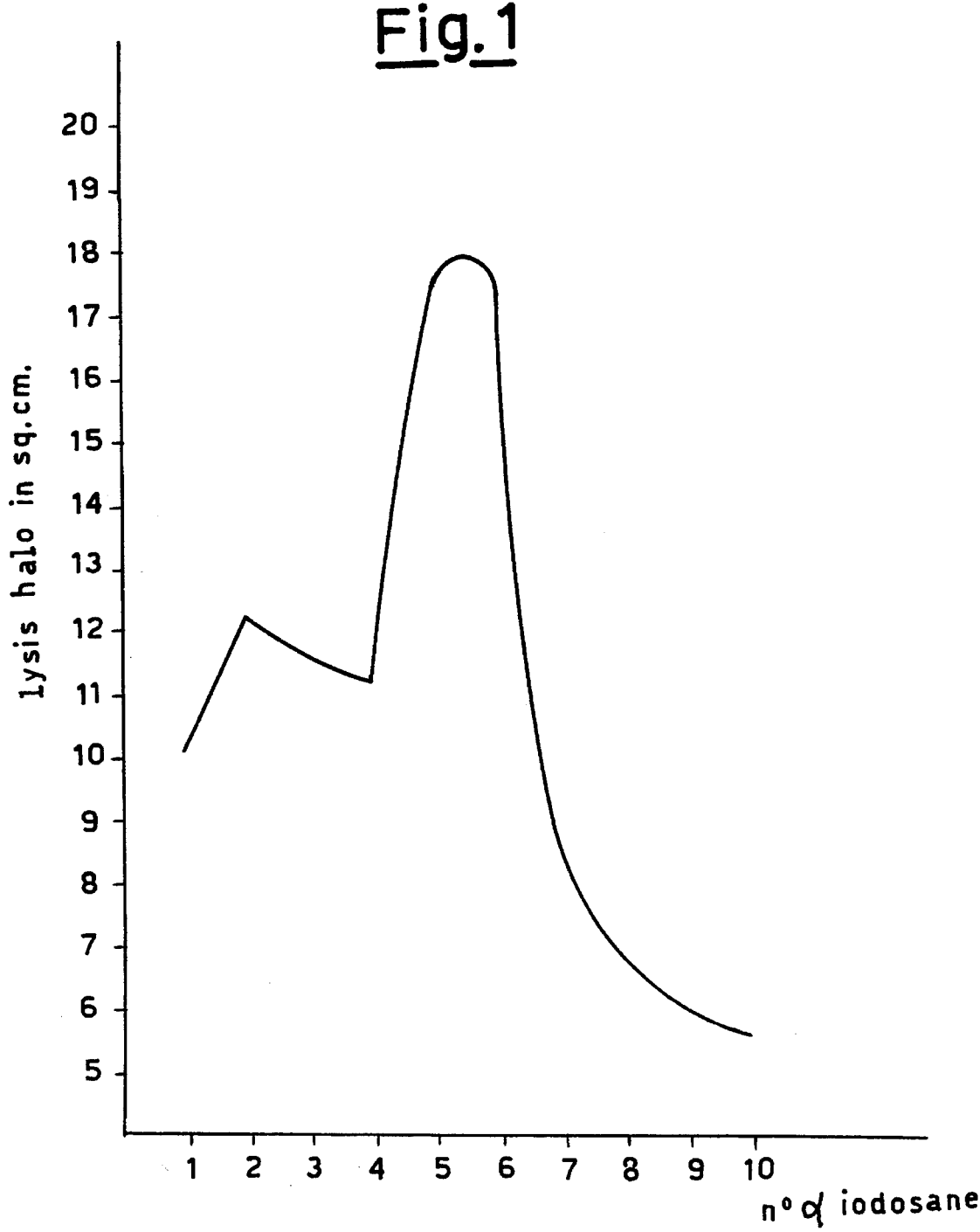
Figure 2:
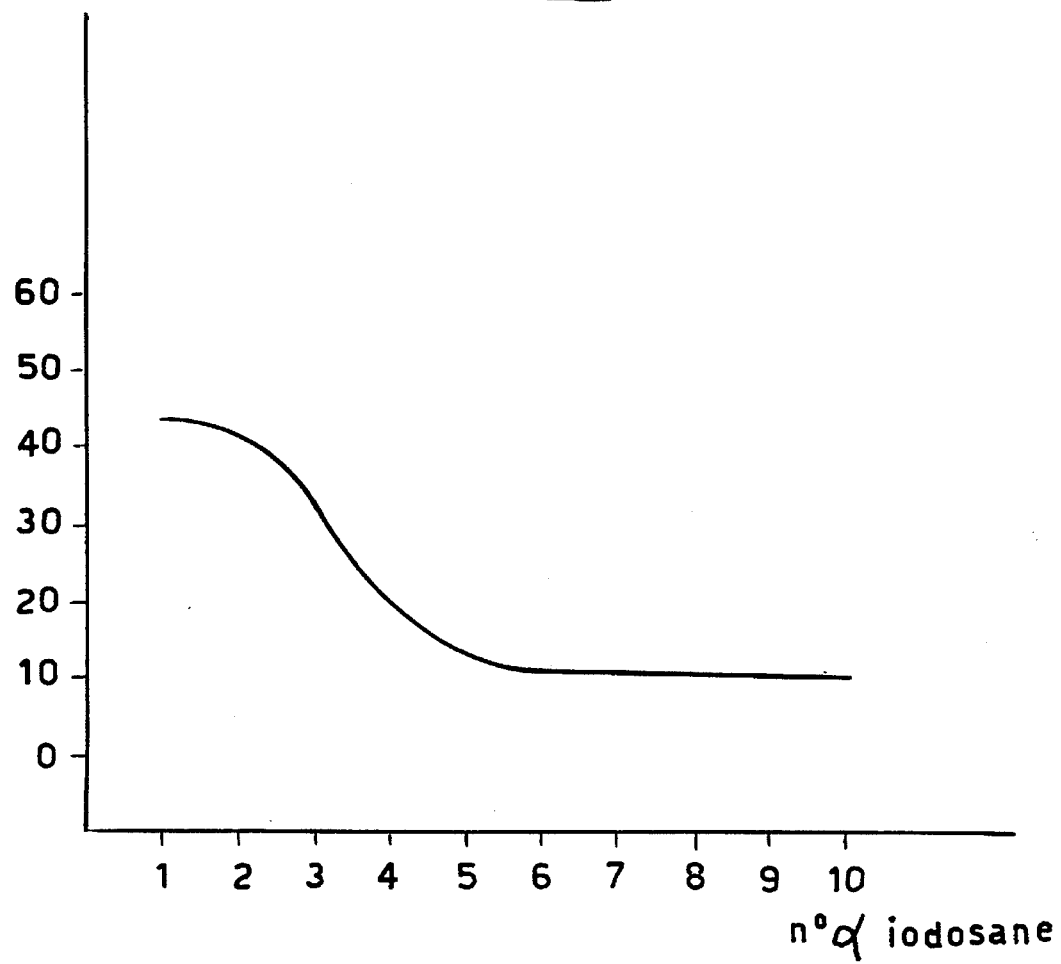

The results thus obtained expressed as a percentage with respect to the increase of the coagulation time induced from heparin taken as 100 are reported in FIG. 2.

The lipasemic activity has been evaluated in the rat in which hyperlipemia had been induced by hyperlipidic diet and by observing the clarifying effect expressed as the D.O. lowering of the plasma 10 minutes after the intravenous administration of the tested compounds.

Figure 3:
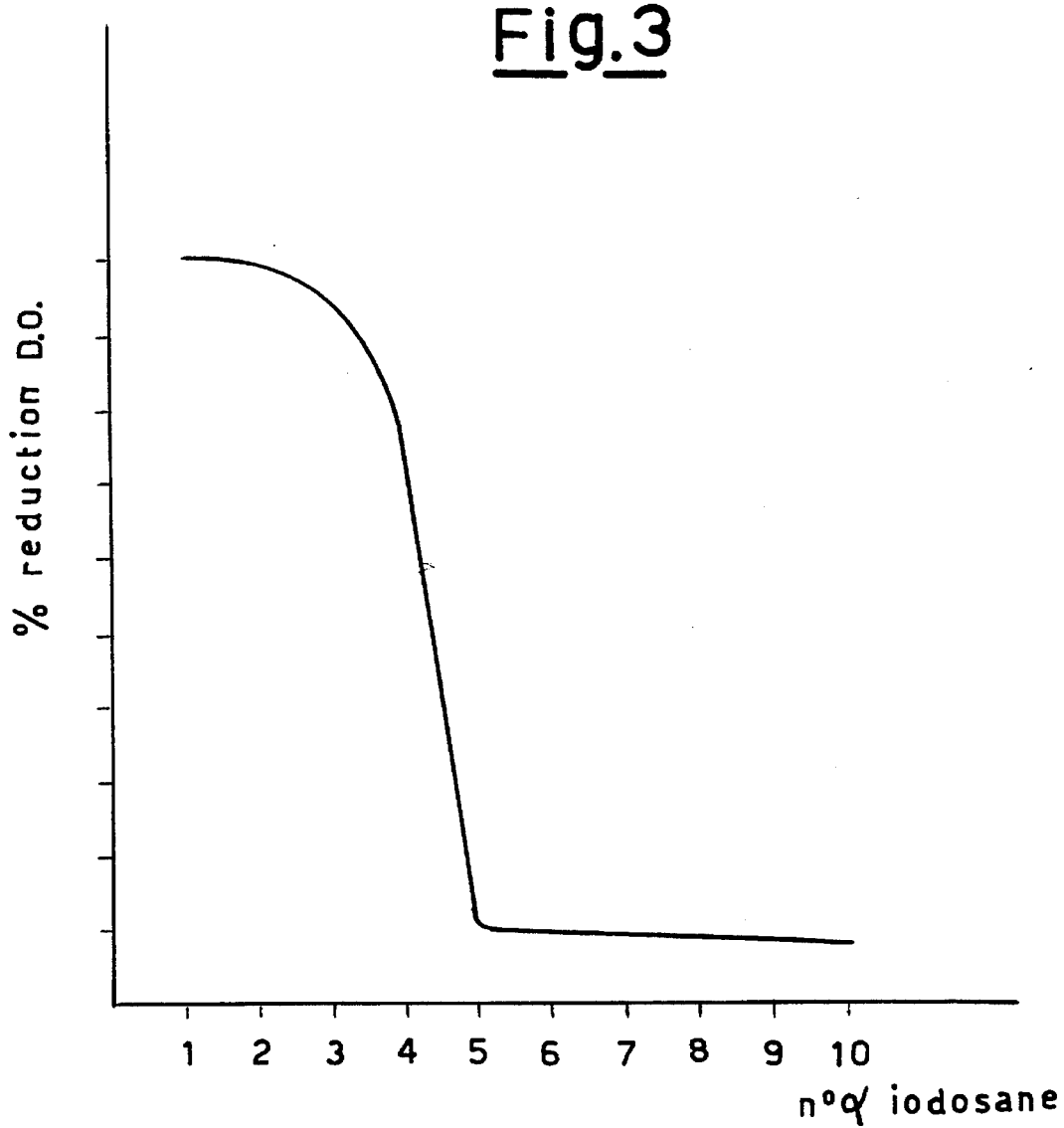

The behaviour of the maximum activity obtained for the several compounds is shown in FIG. 3.

For the 10 alpha-hydosanes of the present invention, the influence on the Anti XA/TT PA ratio has been evaluated in vitro, wherein:

Anti XA=Y in test

TTPA=time of activated partial thromboplastine.

Figure 4:
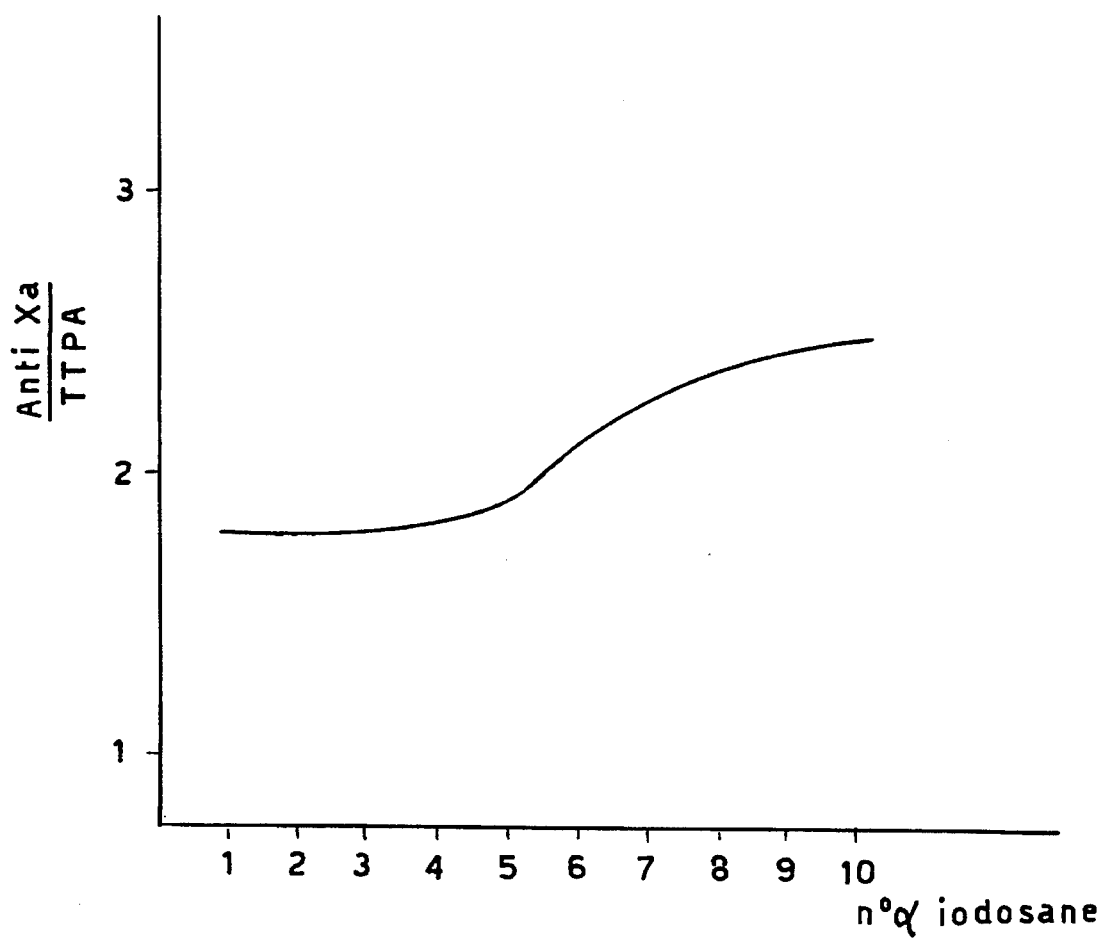

Such a ratio, which for a normal heparin (having m.w.= 15000 and an anticoagulating activity of ≧150 UI/mg) is=1, shows increasing values as the average molecular weight decreases, as it can be observed in FIG. 4.

The interaction of the alpha-hydosanes 5 and 6 with the molecule of plasminogen has been checked by incubating 1 mg/ml of these compounds with plasminogen; the electrophoresis in polyacrylamide gel did not revealed neither diminution of the plasminogen band owing to incubation, nor the appearacne of bands corresponding to the heavy and light chains of the plasmine.

The interaction of the activators of plasminogen has been evaluated in vitro on fibrine platelets containing or not containing the alpha-hydosanes Nos. 5 and 6 and by controlling the influence of their presence on the lysis halo induced from urokinase, streptokinase and from tissutal activator of swine uterus.

It has been thus observed that the alpha-hydosanes 5 and 6 cause an increase of the fibrinolitic activity generated from tissutal activator of swine uterus in a statistically significant manner, whereas in the case of urokinase and streptokinase a slight not significant increase occurs.

According to a further active test, by comparing the alpha-hydosanes Nos. 5 and 6 with fibrine in the absence of plasminogen, it was observed that under these conditions a true lysis is not induced, but only a precipitation halo occurs, which can be probably explained with the forming of structurally defective fibrin.

From the results of the pharmacological experiments the following facts essentially appear:

a) The complex salts of oligosaccharides with metal ions permit a greater physiological availability of the metal to take place.

b) The alpha-hydosanes Nos. 1,2 and 3, having higher average molecular weight are endowed with significant anti-coagulating and lipasemic effect, although lower than those of heparin, relatively lower being the Upasemic one and significatively lower anticoagulating; one these compounds further show, in a lesser degree, effects on the fibrinolithic process and on the Anti Xa/TTPA ratio.

c) The alpha-hydosanes Nos. 5 and 6 show with respect to the other compounds a remarkable interaction with the fibrinolithic process, although it can be seen from the results that such an interaction is not a direct type effect; these compounds have a low interaction with the coagulating process, no interaction with the lipemic situation and a significant interaction with the anti Xa/TTPA ratio.

d) The alpha-hydosanes Nos. 7,8,9 and 10, having lower average molecular weight show a pharmacological profile fully displaced towards an interaction with the Anti Xa/TTPA ratio.

On the basis of the above indication the knowledge has been preliminary increased, by studying the effects induced in volunteers orally or parenterally treated with the several alpha-hydosanes, More particularly:

as regards the alpha-hydosanes 1,2 and 3, volunteer were choosen being affected from dislipemia and from reduced coagulating capacity.

It has been assessed that the treatment with alpha-hydosanes 1,2 and 3, at dosages of between 10 and 100 mg/day for the intramuscular route and of between 50 and 300 mg/day for the oral gastroresistant administration, is able to induce a normalization of the altered physiological parameters (tryglicerides, cholesterol, total lipids, coagulation time etc.) within short treatment periods.

More particularly for the intramuscular route the perfect tolerance, both local and systemic, must be pointed out.

For the alpha-hydosanes 5 and 6, volunteers affected by peripheral venous and arterial thrombosis were selected, The treatment has been carried out at doses of between 5 and 50 mg/day for the intramuscular route and of between 5 and 100 mg/day for the oral gastroresistant administration.

The thrombogenic events are fully solved within short treatment periods without side effects; the local and systemic tolerance after the intramuscular treatment is perfect.

As regards the biochemical parameters, controlled both for the oral and for the parenteral route, it can be observed:

The antithrombine III is increased passing from basel levels of 9 to 10.8 after about 10 days of treatment.

the lysis time of euglobulins decreases in a highly significant manner ready after the first treatment day.

The fibrinogen increases with respect to the basal values for the first 8 to 10 days of treatment, thereafter significatively decreasing therebelow.

the coagulation parameters (coagulation time, hemorrhagy time) generally are not influenced; only in the volunteers having altered values of these parameters, they returned to the physiological levels, without further variations as the treatment prosecuted, The examination of these results indicated a relevant antithrombotic effect of the alpha-hydosanes 5 and 6, which is developed for concomitant reasons, such as the profibrinolithic effect, the interaction with antithrombine III and that with the anti Xa/TTPA ratio, which are proportionally developed both by oral and by parenteral route.

In this sense a confirmation is given by the concomitant fact of an immediate lithic effect not corresponding to an increase of consumption of plasmatic fibrinogen. For the alpha-hydosanes 7,8,9 and 10, volunteers were selected being affected by peripheral venous and arterial thrombosis. The treatment was carried out at doses of between 5 and 100 mg/day for the intramuscular route and of between 10 and 300 mg/day for the oral gastroresistant administration, Within short treatment periods the pathogenesis may be relevantly improved, without inducing side effects, the tolerance both local and systemic, is perfect after the intermuscular administration.

As regards the controlled biochemical parameters a significant effect on the Anti Xa/TTPA ratio is remarkable, together with an activating effect, although not excessive of the fibrinolithic potential and no interaction with the lipemic situation.

We claim:

1. A substantially pure fraction of heparan sulfate having an average molecular weight range of from 12.3 kd to 10.5 kd and fibrinolytic activity, but substantially no anticoagulant activity and no antilipemic activity.

2. A substantially pure fraction of heparan sulfate having an average molecular weight range of from 7.0 kd to 8.6 kd and antithrombolytic activity, but substantially no anticoagulant activity and no antilipemic activity.

3. A substantially pure fraction of heparan sulfate having an average molecular weight range of from 7.0 kd to 13.5 kd and at least one activity selected from the group consisting of fibrinolytic activity and antithrombolytic activity, but substantially no anticoagulant activity and no antilipemic activity.

* * * * *